United States Patent
Smith et al.

(10) Patent No.: US 6,982,346 B2
(45) Date of Patent: Jan. 3, 2006

(54) PROCESS OF MAKING D-PANTHENYL TRIACETATE

(75) Inventors: Jon Kirk Smith, Marion, MA (US); Zongzheng Liu, Fall River, MA (US); Murugappa Vedachalam, Raynham, MA (US); David Compton, Waquoit, MA (US)

(73) Assignee: ISP Investments Inc., Wilmington, DE (US)

( * ) Notice: Subject to any disclaimer, the term of this patent is extended or adjusted under 35 U.S.C. 154(b) by 241 days.

(21) Appl. No.: 10/611,095

(22) Filed: Jul. 1, 2003

(65) Prior Publication Data

US 2005/0002972 A1 Jan. 6, 2005

(51) Int. Cl.
C07C 69/34 (2006.01)
C07C 69/52 (2006.01)
C07C 67/36 (2006.01)

(52) U.S. Cl. .............. 560/190; 560/196; 560/198; 560/204

(58) Field of Classification Search ......... 560/190, 560/196, 198, 204
See application file for complete search history.

(56) References Cited

U.S. PATENT DOCUMENTS 5,415,861 A 5/1995 Duffy et al. ............... 424/401
6,503,515 B1 1/2003 Sterphone et al. ......... 424/401

OTHER PUBLICATIONS

A.R. Prosser and A. J. Sheppard, "Gas-Liquid Chromatographic Determination of Panthothenates and Panthenol", Journal of Pharmaceutical Sciences, vol. 58, No. 6, pp. 718-721 (1969).

*Primary Examiner*—Ba K. Trinh

(74) *Attorney, Agent, or Firm*—William J. Davis; Imre Balogh

(57) ABSTRACT

A process of making D-panthenyl triacetate which includes reacting D-panthenol with acetic anhydride in the presence of the catalyst polymer bound dimethylaminopyridine to form an exothermic mixture. The so-produced acetic acid, and the catalyst are removed from the exothermic mixture which is then neutralized with sodium hydroxide. Sodium acetate in the form of a solid is removed by filtration. The D-panthenyl triacetate is useful in cosmetic compositions.

8 Claims, No Drawings

PROCESS OF MAKING D-PANTHENYL TRIACETATE

BACKGROUND OF THE INVENTION

1. Field of the Invention

The present invention relates to a process of making D-panthenyl triacetate. More particularly, the invention relates to a process of making D-panthenyl triacetate producing an essentially pure and odorless compound that is suitable for use in cosmetic products.

2. Reported Developments

D-panthenyl triacetate is known in the art for use in cosmetic compositions such as face powders, blushes and eye-shadows (see U.S. Pat. Nos. 5,415,861 and 6,503,515).

An article entitled "Gas-Liquid Chromatographic Determination of Pantothenates and Panthenol", A. R. Prosser and A. J. Sheppard, *Journal of Pharmaceutical Sciences*, Vol. 58, No. 6, pp. 718–721 (1969), describes the preparation of triacetate in a 1:1 mixture of acetic anhydride and pyridine.

In cosmetic compositions, it is essential that the ingredients used are essentially pure and odorless and their manufacture is not expensive.

It is an object of the present invention to provide D-panthenyl triacetate inexpensively and in an essentially pure and odorless form for use in cosmetic compositions.

SUMMARY OF THE INVENTION

In accordance with the object of the present invention, a process of making D-panthenyl triacetate is provided comprising the steps of:

a) esterifying D-panthenol with acetic anhydride by mixing D-panthenol, acetic anhydride and the catalyst polymer bound dimethylaminopyridine (P-DMAP) to form an exothermic reaction mixture;
b) completing the reaction;
c) removing acetic acid from the reaction mixture;
d) removing the catalyst from the reaction mixture;
e) neutralizing the reaction mixture with a sodium hydroxide solution; and
f) filtering the solution to obtain D-panthenyl triacetate.

DETAILED DESCRIPTION OF THE INVENTION

The process of making D-panthenyl triacetate is illustrated by the following synthetic step:

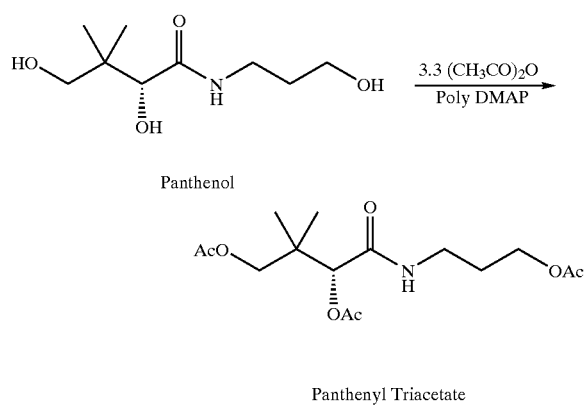

Panthenol

Panthenyl Triacetate

The process comprises the steps described as follows.

D-panthenol is mixed with the catalyst, polymer bound dimethylaminopyridine (P-DMAP), and acetic anhydride to form an exothermic mixture. The mixture is then heated to about 75° C. to 85° C., and preferably 80° C. under atmospheric conditions until analysis indicates that the reaction is complete. The reaction is then pre-stripped at about 85° C. to 100° C. and preferably about 95° C. to decrease the volume of the reaction mixture. The reaction mixture is then cooled to about 65° C. to 75° C., and preferably about 70° C. and transferred through a filter, such as a Niagra filter, to remove the catalyst. (The catalyst may be rinsed with acetic acid and recovered for use in future batches). The reaction mixture is placed under vacuum of less than or equal to 25 mmHg and heated to about 95° C. to 110° C. and preferably to about 105° C. to strip the remaining acetic acid. When the acid level in the reaction mixture is reduced/minimized, it is cooled to about 45° C. to 55° C. and preferably to 50° C. Then sodium hydroxide and a small amount of deionized water are added and the solution is allowed to mix for about 1 to 2 hours. The solution is then transferred through a filter press to remove the sodium acetate and excess sodium hydroxide. The solution is then stripped to remove the remaining water to offer the final product, D-panthenyl triacetate.

Alternatively, acetyl chloride may be used to make the D-panthenyl triacetate without the use of a catalyst. Still another alternative process is to use pyridine as a solvent and a catalyst. These alternative processes are commercially more expensive than using acetic anhydride and polymer bound dimethylaminopyridine.

The reagents used in the process of the present invention are well known and are commercially available.

The following examples illustrate the present invention.

EXAMPLE I

D-panthenol (88 grams, 0.424 moles) and polymer bound dimethylaminopyridine (2 grams) were added to a flask. Acetic anhydride (144.4 grams, 3.3 moles) was slowly added to the stirring mixture, and the resultant exotherm was controlled when the temperature reached 80° C. The mixture was heated at 80° C. and stirred for 9 hours. The flask was then fitted for vacuum distillation, and the acetic acid was removed under reduced pressure to a concentration of about 4% w/w. The catalyst (P-DMAP) was filtered out from the reaction mixture. The solution was treated with a 50% w/w solution of sodium hydroxide in a volume sufficient to neutralize the residual acetic acid, and the resultant solids of sodium acetate were removed by filtration. The residual water was then removed under vacuum to afford about 80% of the desired product, D-panthenyl triacetate.

EXAMPLE II

D-panthenol (177 grams, 0.572 moles) and polymer bound dimethylaminopyridine (2.7 grams) were added to a flask. Acetic anhydride (192.5 grams, 4.4 moles) was slowly added to the stirring mixture, and the resultant exotherm was controlled when the temperature reached 80° C. The mixture was heated at 80° C. and stirred for 9 hours. The flask was then fitted for vacuum distillation, and the acetic acid was removed under reduced pressure to a concentration of about 4% w/w. The catalyst (P-DMAP) was filtered out from the reaction mixture. The solution was treated with a 50% w/w solution of sodium hydroxide in a volume sufficient to neutralize the residual acetic acid, and the resultant solids of sodium acetate were removed by filtration. The residual water was then removed under vacuum to afford about 78% of the desired product, D-panthenyl triacetate.

As can be noted from the above examples, the present invention has the following characteristics:

The catalyst is completely removed from the product by filtration;

The residual acid is removed from the product by treatment with a sodium hydroxide solution, generating the formation of sodium acetate which is filtered from the product avoiding losses normally associated with aqueous extractions;

The use of the catalyst does not result in racemization of the product; The use of the catalyst does not impart any undesirable attributes to the product, such as objectionable odor or toxicity or hazardous conditions; and The use of the catalyst increases the extent of the reaction completion at lower processing temperatures and in a shorter time period.

Various modifications will be apparent to those skilled in the art. Such modifications are within the spirit of the invention limited only by the scope of the claims.

What is claimed is:

1. A process of making D-panthenyl triacetate comprising the steps of:
    a) esterifying D-panthenol in the presence of acetic anhydride and polymer bound dimethylaminopyridine which form an exothermic mixture;
    b) heating the exothermic mixture for a sufficient time to complete the reaction;
    c) removing the acetic acid formed in the exothermic mixture by distillation;
    d) removing the polymer bound dimethylaminopyridine by filtration;
    e) neutralizing the exothermic mixture with a sodium hydroxide solution to precipitate sodium acetate; and
    f) removing the precipitated sodium acetate by filtration.

2. A process of making D-panthenyl triacetate comprising the steps of:
    a) mixing D-panthenol, polymer bound dimethylaminopyridine and acetic anhydride to form an exothermic mixture;
    b) heating the exothermic mixture to about 75° C. to 85° C. under atmospheric conditions to complete the reaction in the exothermic mixture;
    c) pre-stripping the exothermic mixture at about 85° C. to 100° C. to decrease the volume of the exothermic mixture;
    d) cooling the exothermic mixture to about 65° C. to 75° C.;
    e) removing the polymer bound dimethylaminopyridine by filtering the exothermic mixture;
    f) stripping the remaining acetic acid from the exothermic mixture by placing the exothermic mixture under vacuum of less than or equal to 25 mmHg and heating to about 95° C. to 105° C.;
    g) cooling the exothermic mixture to about 45° C. to 55° C.;
    h) neutralizing the exothermic mixture with a sodium hydroxide solution;
    i) removing sodium acetate and excess sodium hydroxide by filtration; and
    j) removing water from the exothermic mixture by stripping to obtain D-panthenyl triacetate.

3. The process of claim 2 wherein the exothermic mixture in step b) is heated to 80° C.

4. The process of claim 2 wherein the exothermic mixture in step c) is heated to 95° C.

5. The process of claim 2 wherein the exothermic mixture in step d) is cooled to 70° C. and filtered to remove the polymer bound dimethylaminopyridine.

6. The process of claim 2 wherein the exothermic mixture in step f) is placed under vacuum and heated to 105° C. to remove acetic acid.

7. The process of claim 2 wherein the exothermic mixture in step g) is cooled to 50° C. and in step h) the exothermic mixture is neutralized with an aqueous solution of sodium hydroxide.

8. A process of making D-panthenyl triacetate comprising the steps of:
    a) mixing D-panthenol with polymer bound dimethylaminopyridine by stirring to obtain a mixture thereof;
    b) adding acetic anhydride to the mixture and heating the mixture to about 80° C.;
    c) removing acetic acid to a concentration of about 4% w/w by vacuum distillation;
    d) removing the polymer bound dimethylaminopyridine by filtration;
    e) neutralizing the mixture with an aqueous sodium hydroxide solution and precipitating sodium acetate therein;
    f) removing the solid sodium acetate by filtration; and
    g) removing residual water from the solution under vacuum to obtain D-panthenyl triacetate.

* * * * *